US006550310B1

(12) United States Patent
Liu et al.

(10) Patent No.: US 6,550,310 B1
(45) Date of Patent: Apr. 22, 2003

(54) CATALYTIC ADSORPTION AND OXIDATION BASED CARBON MONOXIDE SENSOR AND DETECTION METHOD

(75) Inventors: Di-Jia Liu, Naperville, IL (US); Ulrich Bonne, Hopkins, MN (US); Richard A. Alderman, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/724,534

(22) Filed: Nov. 28, 2000

(51) Int. Cl.$^7$ .............................. G01N 7/00; G01N 25/00
(52) U.S. Cl. ...................... 73/31.05; 73/25.05; 73/25.01
(58) Field of Search ............................. 73/31.05, 31.06, 73/31.07, 25.01, 25.05, 23.21, 23.31, 23.32, 204.17

(56) References Cited

U.S. PATENT DOCUMENTS

| | | | |
|---|---|---|---|
| 4,343,768 A | | 8/1982 | Kimura |
| 4,379,402 A | * | 4/1983 | Harman, III ................. 422/52 |
| 4,478,077 A | | 10/1984 | Bohrer et al. |
| 4,501,144 A | | 2/1985 | Higashi et al. |
| 4,624,137 A | | 11/1986 | Johnson et al. |
| 4,651,564 A | | 3/1987 | Johnson et al. |

(List continued on next page.)

FOREIGN PATENT DOCUMENTS

| | | | |
|---|---|---|---|
| GB | 2103806 A | 2/1983 | |
| JP | 63-169547 | 7/1988 | |
| JP | 404047228 A | * 2/1992 | ................. 73/25.01 |

OTHER PUBLICATIONS

Article entitled: "Motorola's MEMS–Based High Performance Carbon–Monoxide Sensor", Jan. 28, 1997.

Article entitled: "New Method for Gas Identification Using a Single Semiconductor Sensor", Takada et al., *Sensors and Actuators B*, 66 (2000) 22–24.

Article entitled: "Fabrication and Properties of a Si–Based High–Sensitivity Microcalorimetric Gas Sensor", Zanini et al., *Sensors and Actuators A*, 48 (1995) 187–192.

Article entitled: "Temperature Drop of Semiconductor Gas Sensor When Exposed to Reducing Gases—Simultaneous Measurement of Changes in Sensor Temperature and in Resistance", Tadashi Takada, *Sensors and Actuators B*, 66 (2000) 1–3.

(List continued on next page.)

*Primary Examiner*—Daniel S. Larkin
*Assistant Examiner*—Michael Cygan
(74) *Attorney, Agent, or Firm*—Kris T. Fredrick

(57) ABSTRACT

A high-sensitivity carbon monoxide sensor is shown and described. The sensor includes a sensing element having a catalyst dispersed over a metal oxide layer. The catalyst is capable of adsorbing carbon monoxide. The sensing element can also include a heater and a temperature sensor. A flow sensor is provided for sensing a flow rate of gas directed at the sensing element. The signal processing module is coupled to the flow sensor and the temperature sensor. A flow sensor sends signals indicative of the flow rate to the processing module while the temperature sensor sends signals indicative of the temperature of the sensing element to the processing module. After carbon monoxide has been adsorbed onto the catalyst and metal oxide layer for a fixed time period, the heater is activated to heat the sensing element above the light-off temperature or at least as high as the oxidation temperature of the adsorbed carbon monoxide. As a result, an exothermic oxidation of the adsorbed carbon monoxide takes place, which results in an increase in the temperature of the sensing element. This increase in the temperature of the sensing element is used to determine the amount of accumulated adsorbed carbon monoxide which, in conjunction with the flow rate and the fixed time period, is used to calculate the carbon monoxide concentration in the gas flow.

32 Claims, 1 Drawing Sheet

U.S. PATENT DOCUMENTS

| | | |
|---|---|---|
| 4,683,159 A | 7/1987 | Bohrer et al. |
| 4,696,188 A | 9/1987 | Higashi |
| 4,914,742 A | 4/1990 | Higashi et al. |
| 4,944,035 A | 7/1990 | Aagardl et al. |
| 4,956,793 A | 9/1990 | Bonne et al. |
| 5,038,304 A | 8/1991 | Bonne |
| 5,177,696 A | 1/1993 | Bonne |
| 5,235,844 A | 8/1993 | Bonne et al. |
| 5,252,949 A | 10/1993 | Kirby et al. |
| 5,351,029 A | 9/1994 | Huth et al. |
| 5,515,714 A * | 5/1996 | Sultan et al. ............ 73/204.18 |
| 5,535,135 A * | 7/1996 | Bush et al. ................. 123/672 |
| 5,629,474 A | 5/1997 | Williams |
| 5,670,949 A * | 9/1997 | Kirby et al. ................ 340/632 |
| 5,813,764 A | 9/1998 | Visseret et al. |
| 5,852,308 A | 12/1998 | Wood |
| 5,861,545 A | 1/1999 | Wood |
| 5,869,749 A | 2/1999 | Bonne et al. |
| 5,892,140 A | 4/1999 | Wood |
| 5,925,476 A | 7/1999 | Kawatsu |
| 5,948,965 A * | 9/1999 | Upchurch et al. ............ 422/88 |
| 6,001,499 A | 12/1999 | Grot et al. |
| 6,071,476 A | 6/2000 | Young et al. |
| 6,090,268 A | 7/2000 | Kunimatsu et al. |
| 6,240,371 B1 * | 5/2001 | Azar ........................... 702/45 |
| 6,318,150 B1 * | 11/2001 | Temple ........................ 432/32 |

OTHER PUBLICATIONS

Article entitled: "Catalytic Calorimetric Gas Sensors", Visser et al., $5^{th}$ Int'l. Mtg. on Chemical Sensors, Rome Italy, Jul. 11–14, 1994 Proceedings, p. 468.

Article entitled: "Design of a Low Power $SnO_2$ Gas Sensor Integrated on Silicon Oxynitride Membrane", Astié et al., *Sensors and Actuators B*, 67 (2000) 84–88.

* cited by examiner

CATALYTIC ADSORPTION AND OXIDATION BASED CARBON MONOXIDE SENSOR AND DETECTION METHOD

TECHNICAL FIELD OF THE INVENTION

The present invention relates generally to gas sensors and, more particularly, to carbon monoxide sensors.

BACKGROUND OF THE INVENTION

Carbon monoxide sensors are used in a wide variety of applications, including the monitoring of heating installations that employ fossil fuels as an energy source and the monitoring of exhaust fumes from internal combustion engines. Two additional applications involve self-cleaning ovens and fuel cells.

Specifically, self-cleaning household ovens include a cleaning cycle that removes carbonaceous residues through a high temperature burning at a high power capacity for a fixed amount of time. Because the high temperature burning consumes a relatively large quantity of energy, there is a need for efficient self-cleaning cycles that automatically shut the oven off as soon as the burning process is complete. One way to accomplish this would be to monitor the carbon monoxide evolution during the heating cycle. Specifically, it is known that a typical dirty oven, when being cleaned at temperatures exceeding 800° F., will begin to emit carbon monoxide at a temperature of about 550° F. The amount of carbon monoxide being emitted will peak at around 800° F. at a value of about 1500 ppm. After this peak value is reached, the carbon monoxide concentration decreases to around 200 ppm at the end of the cycle. An appropriate shut down point will occur for a typical household oven at a carbon monoxide concentration of about 200 ppm.

Therefore, there is a need for a robust, high-sensitivity carbon monoxide sensor to monitor self-cleaning oven cycles. The sensor must be sufficiently robust to withstand temperatures of 400° F. or more. Further, the sensor must be sensitive enough to detect a relatively low concentration of carbon monoxide of less than 50 ppm.

Currently-available carbon monoxide sensors include infrared adsorption sensors and thin metal film metal oxide technology, such as tin oxide sensors. The infrared adsorption sensors are inappropriate for the household oven market due to their high cost and low sensitivity. The thin metal film oxide sensors are also inappropriate for use in monitoring self-cleaning oven cycles because they generally do not work well in a humid environment. Further, metal oxide sensors take a long time to regenerate.

Accordingly, there is a need for a low-cost, fast-response and high-sensitivity carbon monoxide sensor for use in self-cleaning ovens and other devices.

As noted above, another application for carbon monoxide sensors is in connection with fuel cells. Fuel cells are known devices that convert chemical energy of a fuel to electrical energy. Each fuel cell includes a pair of electrodes arranged across an electrolyte.

For proton exchange membrane fuel cells, the surface of one electrode is exposed to hydrogen or a hydrogen-containing gaseous fuel and the surface of the other electrode is exposed to an oxygen-containing, oxidizing gas. Electrical energy is produced at the electrodes through electrochemical reactions. Typically, a catalyst is used on the surface of the anode that is exposed to hydrogen or the hydrogen-containing gaseous fuel. One known problem associated with fuel cells is the deactivation of this catalyst by the adsorption of carbon monoxide which is present in trace amounts in hydrogen containing reformate fuel.

Therefore, there is also a need for a high sensitivity carbon monoxide sensor for monitoring the carbon monoxide level of the hydrogen or hydrogen-containing gaseous fuel fed to the anodes of a fuel cell. Again, existing infrared sensors are undesirable due to their high cost and low sensitivity and thin-film metal oxide sensors are disadvantageous due to their slow regeneration time and the instability in humidified environments. Thus, there is a need for a high sensitivity and economical carbon monoxide sensor for monitoring the concentration of carbon monoxide in the hydrogen-containing fuel fed to the anodes of a fuel cell.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

In accordance with one aspect of the present invention, a carbon monoxide sensor comprises a sensing element that, in turn, comprises a catalyst dispersed over a metal oxide layer. The catalyst is capable of adsorbing carbon monoxide onto the metal oxide layer. The sensing element further comprises a temperature sensor. A flow sensor is provided for sensing the flow rate of gas directed at the sensing element. A signal processing module is coupled to both the flow sensor and the temperature sensor. The flow sensor sends signals indicative of the flow rate to the processing module and the sensing element sends signals indicative of the temperature of the sensing element to the processing module.

In a dependent refinement of this first aspect, after carbon monoxide has been adsorbed and accumulated onto the metal oxide layer, a heater heats the sensing element to a first temperature that is at least as high as the oxidation temperature of the carbon monoxide that has been adsorbed onto the first metal oxide layer, thereby resulting in an exothermic oxidation of the carbon monoxide adsorbed onto the first metal oxide layer and an increase in temperature of the sensing element to a second higher temperature. This temperature increase caused by the oxidation of the carbon monoxide provides an indication of the presence of carbon monoxide and, as discussed further below, in combination with the flow sensor signal, provides a basis for calculating the concentration of the carbon monoxide.

In other dependent refinements of this first aspect, the catalyst is selected from the group consisting of silver, gold, rhodium, ruthenium, palladium, iridium, platinum, metallic alloys of these elements and mixtures thereof. Presently, the preferred catalysts are platinum, ruthenium, ruthenium platinum alloys and ruthenium iridium alloys. The metal oxide layer can be a refractory metal oxide such as alumina, silica, titania and zirconia.

In further dependent refinements of this first aspect, a filter is provided upstream of the sensing element for purposes of keeping the sensing element clean and free of contaminants and foulants. Preferably, the filter is also disposed upstream of the flow rate sensor for purposes of protecting this component as well. In a further dependent refinement, the catalyst of the sensing element is a first catalyst and the metal oxide layer of the sensing element is a first metal oxide layer. In such a refinement, the sensing element can also include a protective second metal oxide layer disposed on top of the first catalyst and first oxide layer. The second metal oxide layer can be nickel oxide, zinc oxide or manganese dioxide. Other metal oxides will be suitable as well.

In accordance with another aspect of the present invention, a reference sensing element can also be provided as a part of the carbon monoxide sensor. The reference sensing element comprises the catalyst dispersed over a layer of the metal oxide. The reference sensing element also includes a heater and a temperature sensor. However, the reference sensing element is disposed downstream of a low temperature carbon monoxide oxidation catalyst that is dispersed on a substrate so that all gas that reaches the reference sensing element interacts with the low temperature carbon monoxide oxidation catalyst supported on the substrate. Accordingly, the low temperature carbon monoxide oxidation catalyst dispersed on the substrate is intended to oxidize all carbon monoxide before it reaches the reference sensing element. Thus, the reference temperature sensor of the reference sensing element provides a base line value which is communicated to the processing module. In a preferred embodiment, the catalyst of the reference sensing element is the same as the first catalyst and the oxide layer is the same as the first metal oxide layer.

In accordance with another aspect of the present invention, a method of detecting the presence of carbon monoxide in a gas is provided. The method includes exposing a catalyst dispersed on a metal oxide layer to a gas that comprises carbon monoxide. The catalyst is capable of adsorbing carbon monoxide onto the first metal oxide layer. The method also includes adsorbing at least a portion of the carbon monoxide in the gas onto the metal oxide layer below the carbon monoxide oxidation temperature. The method further includes heating the metal oxide layer to a first temperature that is at least as high as the oxidation temperature of the carbon monoxide adsorbed onto the metal oxide layer, thereby resulting in an exothermic oxidation of the carbon monoxide adsorbed onto the metal oxide layer and an increase in the temperature of the first metal oxide layer. The method further includes recording the temperature increase of the metal oxide layer, thereby indicating a presence of carbon monoxide in the gas.

In accordance with another aspect of the present invention, the aforenoted method further includes sensing a flow rate of gas that engages the catalyst and metal oxide layer over a fixed time period. Such a method also includes calculating a cumulative value for the carbon monoxide adsorbed onto the metal oxide layer from the increase in temperature of the metal oxide layer due to the exothermic oxidation of the carbon monoxide. Such a method would also include calculating a volume of gas by multiplying the flow rate by the fixed time period. The method also includes calculating the concentration of carbon monoxide in the gas by dividing the cumulative value by the volume.

In accordance with another aspect of the present invention, the aforenoted method can also include providing a reference cumulative value by providing a reference sensing element comprising the catalyst dispersed over a layer of the metal oxide and by providing a second catalyst supported on a substrate. The second catalyst and substrate would be disposed upstream of the reference sensing element so that it interacts with all gas that reaches the reference sensing element. The second catalyst would be a low temperature carbon monoxide catalyst which would thereby oxidize substantially all carbon monoxide in the gas that reaches the reference sensing element. The method would also include heating the reference sensing element to the first temperature simultaneously with the heating of the first sensing element, recording any temperature change of the reference sensing element from the first temperature, generating a reference value from the temperature change and reducing the cumulative value for the carbon monoxide detected by the first sensing element by subtracting the reference value.

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the scope of the invention will become apparent to those of skill in the art from the detailed description of the invention and claims that follow.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

It should be understood that the drawings are not necessarily to scale and that the embodiments are illustrated using graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE INVENTION

Figure 1:
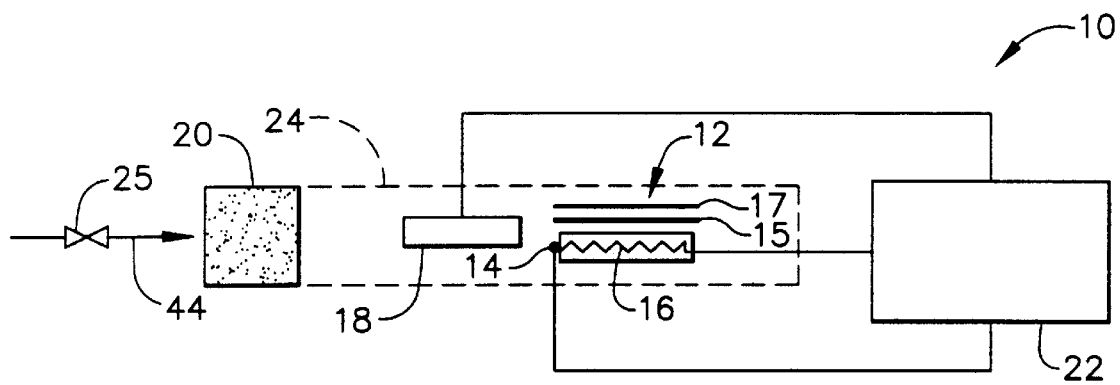
FIG. 1 is a schematic illustration of a carbon monoxide sensor made in accordance with the present invention.

Turning to FIG. 1, a carbon monoxide sensor 10 is illustrated which includes a sensing element 12 that includes a temperature probe or sensor 14, a catalyst/metal oxide layer 15, a heater 16 and a protective layer 17. A flow sensor 18 provides a volumetric measurement of the gas directed toward the sensor 12. A filter 20 is provided to protect the flow sensor 18 and sensing element 12 from contaminants and foulants. The temperature sensor 14, the heater 16 and the flow sensor 18 are coupled to a processing module 22.

The gas stream to be measured flows in the direction of the filter 20 as shown by the arrow 44. If carbon monoxide is present in the gas stream, the carbon monoxide will be adsorbed onto the first catalyst/metal oxide layer 15 of the sensing element 12. Periodically, the processing module 22 will activate the heater 16 to heat the sensing element 12 to a first temperature above the ambient temperature. The first temperature is at least as high as the catalytic oxidation temperature of the adsorbed carbon monoxide, thereby resulting in an exothermic oxidation of the adsorbed carbon monoxide and a further increase in temperature of the sensing element 12 to a second temperature, which is higher than the first temperature.

The amount of carbon monoxide accumulated or adsorbed on the sensing element surface ($CO_{ACC}$) is proportional to the carbon monoxide concentration ($C_{CO}$), the flow rate (F) and the time period of the duty cycle (t) as expressed by the following equation:

$$CO_{ACC} \ C_{CO}*F*t \tag{1}$$

The amount of CO adsorbed by the sensing element 12 ($CO_{ACC}$) is proportional to the integration of the increasing temperature as a function of time. Accordingly, with $CO_{ACC}$ known, the carbon monoxide concentration in the flow stream can be calibrated by dividing the value for the carbon monoxide accumulation by the flow rate and time period.

It will be noted that if the carbon monoxide concentration ($C_{CO}$) is too high, the catalyst metal oxide layer will become saturated. The embodiment of the current design avoids this situation by shortening the duty cycle (t) through the processing module 22 so that the sensing element 12 will be heated to the first temperature after a shortened adsorption period and before the saturation can occur. In the alternative, the flow rate can be controlled or, in this case, reduced to avoid catalyst saturation. It is also foreseeable that the duty cycle (t) and flow rate (F) may need to be increased in the event of a low carbon monoxide concentration.

Figure 2:
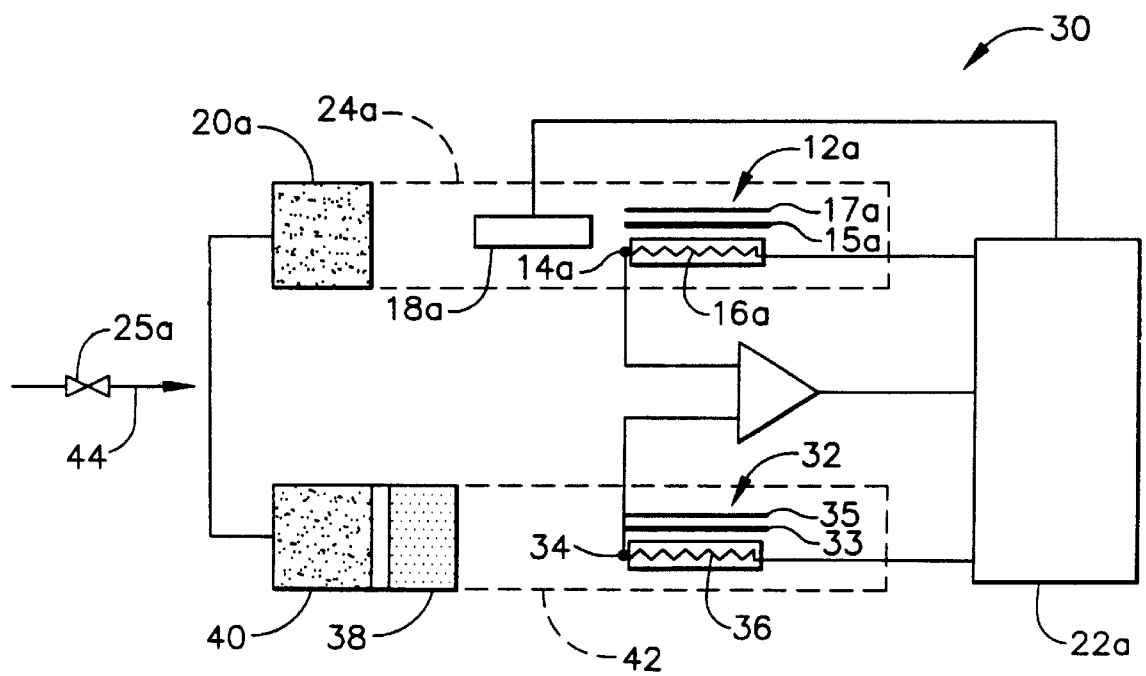
FIG. 2 is a schematic illustration of another embodiment of the carbon monoxide sensor of the present invention.

Accordingly, a closed loop control of the sensor 10 varies the duty cycle (t) and/or the flow rate (F) depending upon the carbon monoxide concentration in the gas stream. Further, an alternative embodiment fixes the flow rate (F). In order to vary the flow rate (F), a valve 25 is shown in FIG. 1 and a valve 25a is shown in FIG. 2. The combination of both duty cycle and flow rate control has greatly expanded the detection range of carbon monoxide concentration from 1 ppm to over 10,000 ppm.

The catalyst used for the catalyst/metal oxide layer 15 of the sensing element 12 can be platinum, palladium, ruthenium, iridium, rhodium, metallic alloys of these metals and mixtures thereof. The inventors have found these catalysts are highly selective to the adsorption carbon monoxide in the presence of excess carbon dioxide. Furthermore, they are also very effective catalysts for the oxidation of carbon monoxide when the sensor is above the catalytic oxidation temperature. The metal oxide is preferably alumina, silica, titania or zirconia or other refractory metal oxides with high specific surface area. The preferred specific surface area ranges from about 10 $m^2/g$ to about 300 $m^2/g$. A protective cover layer 17 can also be provided in the form of a metal oxide such as nickel oxide, zinc oxide or manganese dioxide. The main purpose of the protective cover layer 17 is to protect the precious metal catalysts in sub-layer 15 from poisoning by gas phase sulfur and phosphorous based contaminants. Therefore, the accuracy and lifetime are significantly improved. The thickness of each metal oxide layer can range from less than one to five micrometers.

In the preferred embodiment, the temperature sensor 14 and flow sensor 18 are micro-bridge structures due to their small size, low cost and high reliability. The details of the micro-bridge structures will not be repeated here as they are well known to those skilled in the art. The heating element 16 is a resistive element which can heat the surface of the sensing element 12 from ambient or room temperature to 120° C. within 100 microseconds. Coupled with the processing module 22, the heating element 16 can also change the temperature of the surface of the sensing element 12 within an accuracy of +/−0.01° C. The filter 20 is a standard particle filter installed upstream to remove contaminants and foulants, such as residues and high boiling point grease. The housing 24 is shown in phantom.

During use, the gas flow containing carbon monoxide, carbon dioxide and other gas components passes through the sensing element 12 after it has passed through the filter 20 and flow sensor 18. During the adsorption cycle, the temperature of the sensing element 12 is maintained at ambient temperature or below 70° C. The carbon monoxide in the gas interacts with the precious metal catalyst on the sensing element 12 by forming a quasi-chemical bond through a chemisorption process. The chemisorption of carbon monoxide over catalyst described in the embodiment of this invention has high Gibbs free energy of adsorption ranging from 20 to 35 kcal/mol. Therefore, the chemisorbed carbon monoxide is very stable, which allows for the continuous accumulation of carbon monoxide on the sensing element 12 even if the gas phase concentration of carbon monoxide is in the range of a few ppm. This process greatly enhances the detection sensitivity toward the gas phase carbon monoxide concentration.

After the sensing element 12 has been exposed to the gas flow containing carbon monoxide for a fixed time period or duty cycle, the temperature of the sensing element 12 is heated from ambient temperature to over 100° C. or to a temperature which is higher than the catalytic light-off temperature of carbon monoxide oxidation over the catalyst surface. This temperature can range from 100° C. to 150° C. Carbon monoxide oxidation is a strong exothermic process and occurs rapidly with the pre-adsorbed carbon monoxide. For example, the carbon monoxide sensor 10 made in accordance with the present invention with a 100 micrometer×200 micrometer surface area and a 2 micrometer catalyst/first metal oxide layer thickness and a 10 percent platinum loading will result in a temperature increase during the carbon monoxide oxidation with a fully saturated surface of approximately 60° C. This temperature change well exceeds the micro-bridge temperature sensor 14 detection sensitivity which is as low as 0.02° C. Consequently, the sharp temperature increase of the sensing element 12 can be detected by the temperature sensor 14, which can be of a micro-bridge design. The integration of the electric signal output from the temperature sensor 14 can be correlated with the carbon monoxide concentration in the gas mixture as shown above. To avoid slow drift of the sensitivity of the carbon monoxide sensor 10 due to build-up of undesirable contaminants at the surface of the sensing element 12, the carbon monoxide sensor 10 can be periodically regenerated through controlled heating by the built-in heating element 16 which, preferably, is disposed on the micro-bridge chip. The heated regeneration can be operated above 200° C. or other suitable temperature for a brief period of time before the carbon monoxide sensor 10 is ready for another period of operation.

Turning to FIG. 2, an alternative embodiment of the present invention is illustrated by way of a carbon monoxide sensor 30 to further enhance the sensor sensitivity by subtracting out common mode noise and interference caused by humidity and other potential interfering agents. The carbon monoxide sensor 30 includes a sensing element 12a equipped with a heating element 16a, temperature probe 14a, catalyst/metal oxide layer 15a, protective layer 17a, flow sensor 18a, filter 20a, housing 24a and valve 25a as discussed above in connection with FIG. 1. Similarly, the flow sensor 18a, temperature sensor 14a and heater 16a are coupled to the processing module 22a. However, a reference sensing element 32 is also provided, which includes a temperature sensor 34 and heater 36. The reference sensing element 32 has the same construction as the sensing element 12a. That is, it includes a precious metal catalyst dispersed over a refractory metal oxide in the layer 33 and, preferably, includes a protective top metal oxide layer 35. However, disposed upstream of the reference sensing element 32 is a low temperature CO oxidation catalyst 38 supported on a monolithic substrate that includes a low temperature carbon monoxide oxidation catalyst. A filter is provided at 40. Thus, prior to reaching the reference sensing element 32, gas flows through the filter 40 and through the low temperature carbon monoxide oxidation catalyst 38 dispersed thereon. As a result, all of the carbon monoxide in the gas flow should be oxidized prior to reaching the reference sensing element 32. The low temperature carbon monoxide oxidation catalyst 38 can be a noble metal catalyst such as gold or palladium supported on gamma alumina, or metal oxide catalysts such as Hopcalite. The substrate can be a high cell density ceramic monolith, as is known to those skilled in the art. The reference sensing element 32 is operated in the same fashion as the carbon monoxide sensing element 12a. The signal generated by the reference sensing element 32 will preferably be subtracted from the signal generated by the carbon monoxide sensing element through differential amplification although other operations can be employed as will become apparent to those skilled in the art. The main function of the reference sensing element 32 is to remove the interference from adsorbed moisture during the carbon monoxide adsorption process and the common mode noise and the drift. Similar to the carbon monoxide sensing element 12a, the reference sensing element 32 is contained, along with the filter 40 and low temperature carbon monoxide oxidation catalyst substrate 38 in a common housing 42. The direction of the gas flow is indicated by the arrow 44.

As noted above, the micro-bridge construction of the temperature sensors 14, 14a, 34, the flow sensors 18, 18a and the heater controls are known to those skilled in the art of microelectromechanical systems (MEMS) technology.

It will be noted that the sensors of the present invention are operable only when oxygen is present.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A carbon monoxide sensor comprising:
   a sensing element;
   a flow sensor for sensing a flow rate of gas towards the sensing element;
   a signal processing module in communication with the flow sensor and the sensing element;
   the sensing element comprising a catalyst dispersed over a metal oxide layer, the catalyst capable of adsorbing carbon monoxide onto the metal oxide layer;
   the flow sensor sending a signal indicative of the flow rate to the processing module;
   the sensing element sending a signal indicative of the temperature of the sensing element to the processing module;
   the processing module measuring the carbon monoxide in accordance with the flow rate signal and the temperature signal.

2. The carbon monoxide sensor of claim 1 further comprising a heater wherein, after carbon monoxide has been adsorbed onto the metal oxide layer, the heater heats the sensing element to a first temperature that is at least as high as the oxidation temperature of carbon monoxide adsorbed onto the metal oxide layer, thereby resulting in an exothermic oxidation of said carbon monoxide adsorbed onto the metal oxide layer and an increase in temperature of the sensing element to a second temperature.

3. The carbon monoxide sensor of claim 2 wherein the heater is capable of heating the sensing element to a third temperature of at least 200° C. for regenerating the catalyst.

4. The carbon monoxide sensor of claim 1 wherein the processing module determines accumulated carbon monoxide $CO_{ACC}$ in accordance with the increase in temperature and, wherein the processing module determines carbon monoxide concentration $C_{CO}$ in accordance with the following equation:

$$CO_{ACC} \; C_{CO}*F*t$$

where F is the flow rate signal and t is time.

5. The carbon monoxide sensor of claim 1 wherein the catalyst is selected from the group consisting of Ag, Au, Ru, Rh, Pd, Ir, Pt, metallic alloys thereof and mixtures thereof.

6. The carbon monoxide sensor of claim 1 wherein the catalyst comprises Pt.

7. The carbon monoxide sensor of claim 1 wherein the catalyst comprises Ru.

8. The carbon monoxide sensor of claim 1 wherein the catalyst comprises a RuPt alloy.

9. The carbon monoxide sensor of claim 1 wherein the catalyst comprises a RuIr alloy.

10. The carbon monoxide sensor of claim 1 wherein the metal oxide layer comprises at least one refractory metal oxide.

11. The carbon monoxide sensor of claim 1 wherein the metal oxide layer comprises a metal oxide selected from the group consisting of alumina, silica, titania and zirconia.

12. The carbon monoxide sensor of claim 1 further comprising a filter disposed upstream of the sensing element.

13. The carbon monoxide sensor of claim 1 further comprising a filter disposed upstream of the flow rate sensor so that the flow rate sensor is disposed between the filter and the sensing element.

14. The carbon monoxide sensor of claim 1 wherein the metal oxide layer is a first metal oxide layer and the sensing element further comprises a second metal oxide layer disposed on top of the catalyst and the first metal oxide layer.

15. The carbon monoxide sensor of claim 14 wherein the second metal oxide layer comprises a metal oxide selected from the group consisting of NiO, ZnO and $MnO_2$, and mixtures thereof.

16. The carbon monoxide sensor of claim 1 further comprising a reference sensing element comprising the catalyst dispersed over a layer of the metal oxide, the reference sensing element further comprising a heater;
   the carbon monoxide sensor further comprising a low temperature carbon monoxide oxidation catalyst dispersed on a substrate, the low temperature carbon monoxide oxidation catalyst and substrate being disposed upstream of the reference sensing element;

the reference sensing element being coupled to the processing module.

17. A method of detecting a presence of carbon monoxide in a gas comprising the following steps:

exposing a catalyst dispersed onto a metal oxide layer to the gas that comprises carbon monoxide, the catalyst capable of adsorbing carbon monoxide onto the metal oxide layer;

adsorbing at least a portion of the carbon monoxide in the gas onto the metal oxide layer;

heating the catalyst and metal oxide layer to a first temperature that is at least as high as the oxidation temperature of carbon monoxide adsorbed onto the first metal oxide layer, thereby resulting in an exothermic oxidation of said carbon monoxide adsorbed onto the metal oxide layer and an increase in temperature of the metal oxide layer;

using the temperature increase of the metal oxide layer, thereby indicating the presence of carbon monoxide in the gas.

18. The method of claim 17 wherein the catalyst and metal oxide layer form part of a sensing element that further comprises a heater for heating the metal oxide layer.

19. The method of claim 18 wherein a signal processing module is coupled to the sensing element.

20. The method of claim 17 further comprising the steps of:

sensing a flow rate of gas that engages the catalyst and metal oxide layer over a fixed time period;

calculating a cumulative value for the carbon monoxide adsorbed onto the metal oxide layer from the increase in temperature of the metal oxide layer due to the exothermic oxidation of the carbon monoxide;

calculating a volume of gas by multiplying the flow rate by the fixed time period;

calculating a concentration of carbon monoxide in the gas as a function of the cumulative value and the volume.

21. The method of claim 20 wherein the catalyst is a first catalyst, wherein the method further comprises the step of providing a reference cumulative value provided by a reference sensing element comprising the first catalyst dispersed over a layer of the metal oxide, and by providing a second catalyst dispersed on a substrate, the second catalyst and substrate being disposed upstream of the reference sensing element, the second catalyst being a low temperature carbon monoxide catalyst which thereby oxidizes substantially all carbon monoxide in the gas that reaches the reference sensing element;

heating the reference sensing element to the first temperature;

recording any temperature increase of the reference sensing element above the first temperature;

calculating a reference value from said temperature increase;

reducing the cumulative value for the carbon monoxide gas by the reference cumulative value.

22. The method of claim 21 wherein the reducing step is performed by differential amplification.

23. The method of claim 17 wherein the catalyst is selected from the group consisting of Ag, Au, Ru, Rh, Pd, Ir, Pt, metallic alloys thereof and mixtures thereof.

24. The method of claim 17 wherein the metal oxide layer comprises at least one refractory metal oxide.

25. The method of claim 17 wherein the metal oxide layer comprises a metal oxide selected from the group consisting of alumina, silica, titania and zirconia, and mixtures thereof.

26. The method of claim 17 further comprising the step of filtering the gas before it reaches the metal oxide layer.

27. The method of claim 17 further comprising the step of regenerating the catalyst by heating the catalyst and metal oxide layer to a temperature of at least 200° C.

28. A carbon monoxide sensor comprising:

a sensing element;

a flow sensor for sensing a flow rate of gas towards the sensing element;

a filter disposed upstream of the flow rate sensor so that the flow rate sensor is disposed between the filter and the sensing element;

a signal processing module in communication with the flow sensor and the sensing element;

the sensing element comprising a catalyst dispersed over a first metal oxide layer, the catalyst capable of adsorbing carbon monoxide onto the first metal oxide layer, the sensing element further comprising a second metal oxide layer disposed on top of the catalyst and first oxide layer, the sensing element further comprising a heater;

the flow sensor sending signals indicative of the flow rate to the processing module;

the sensing element sending signals indicative of the temperature of the sensing element to the processing module;

whereby, after carbon monoxide has been adsorbed onto the first metal oxide layer, the heater heats the sensing element to a first temperature that is at least as high as the oxidation temperature of carbon monoxide adsorbed onto the first metal oxide layer, thereby resulting in an exothermic oxidation of said carbon monoxide adsorbed onto the first metal oxide layer and an increase in temperature of the sensing element to a second temperature.

29. The carbon monoxide layer of claim 28 wherein the first metal oxide has a surface area ranging from about 50 $m^2/g$ to about 300 $m^2/g$.

30. The carbon monoxide sensor of claim 28 further comprising a reference sensing element and, the reference sensing element comprising the catalyst dispersed over a layer of the first metal oxide, the reference sensing element further comprising a heater;

the carbon monoxide sensor further comprising a low temperature carbon monoxide oxidation catalyst dispersed on a substrate, the low temperature carbon monoxide oxidation catalyst and substrate being disposed upstream of the reference sensing element;

the reference sensing element being coupled to the processing module.

31. A method of detecting a presence of carbon monoxide in an exhaust stream comprising the following steps:

exposing a catalyst dispersed onto a metal oxide layer to the exhaust stream, the catalyst capable of adsorbing carbon monoxide onto the metal oxide layer;

adsorbing at least a portion of the carbon monoxide in the exhaust stream onto the metal oxide layer;

sensing a flow rate of the exhaust stream that engages the catalyst and metal oxide layer over a fixed time period;

heating the metal oxide layer to a first temperature that is at least as high as the oxidation temperature of carbon monoxide adsorbed onto the metal oxide layer, thereby resulting in an exothermic oxidation of said carbon monoxide adsorbed onto the metal oxide layer and an increase in temperature of the metal oxide layer;

using the temperature increase of the metal oxide layer, thereby indicating the presence of carbon monoxide in the exhaust stream;

calculating a cumulative value for the carbon monoxide adsorbed onto the metal oxide layer from the increase in temperature of the metal oxide layer due to the exothermic oxidation of the carbon monoxide;

calculating a volume of exhaust stream by multiplying the flow rate by the fixed time period;

calculating a concentration of carbon monoxide in the exhaust stream as a function of the cumulative value and the volume.

32. The method of claim 31 wherein the catalyst is a first catalyst, and wherein the method further comprises the step of providing a reference cumulative value by providing a reference sensing element comprising a second catalyst dispersed over a second metal oxide, and by providing a third catalyst dispersed on a substrate, the third catalyst and substrate being disposed upstream of the reference sensing element, the third catalyst being a low temperature carbon monoxide catalyst which thereby oxidizes substantially all carbon monoxide in the exhaust stream that reaches the reference sensing element;

heating the reference sensing element to the first temperature;

recording any temperature increase of the sensing element above the first temperature;

calculating a reference value from said temperature increase;

reducing the cumulative value for the carbon monoxide exhaust stream by the reference value.

* * * * *